United States Patent
Wright, III

(10) Patent No.: US 7,185,545 B2
(45) Date of Patent: Mar. 6, 2007

(54) INSTRUMENTATION AND METHOD FOR MONITORING CHANGE IN ELECTRIC POTENTIAL TO DETECT CRACK GROWTH

(75) Inventor: Philemon Kennard Wright, III, Easton, MD (US)

(73) Assignee: General Electric Company, Schenectady, NY (US)

( * ) Notice: Subject to any disclaimer, the term of this patent is extended or adjusted under 35 U.S.C. 154(b) by 84 days.

(21) Appl. No.: 11/025,513

(22) Filed: Dec. 29, 2004

(65) Prior Publication Data
US 2006/0137466 A1 Jun. 29, 2006

(51) Int. Cl.
G01N 19/08 (2006.01)
G01N 29/07 (2006.01)
G01R 27/08 (2006.01)

(52) U.S. Cl. .......................... 73/799; 73/788; 73/775; 73/774; 324/716; 324/717; 324/718

(58) Field of Classification Search .................. 73/808, 73/775, 772, 763, 768, 774, 799, 762, 835; 324/718, 716, 717, 723, 715
See application file for complete search history.

(56) References Cited

U.S. PATENT DOCUMENTS

| | | | | |
|---|---|---|---|---|
| 3,738,162 A * | 6/1973 | Dally et al. | .................... | 73/775 |
| 3,805,601 A * | 4/1974 | Jeffers | .......................... | 73/777 |
| 3,918,299 A * | 11/1975 | Donnadieu | .................... | 73/772 |
| 4,003,246 A * | 1/1977 | Cain | .......................... | 73/799 |
| 4,151,502 A * | 4/1979 | Kurihara et al. | ................ | 338/2 |
| 4,677,855 A | 7/1987 | Coffin, Jr. et al. | | |
| 4,816,800 A | 3/1989 | Onaga et al. | | |

(Continued)

FOREIGN PATENT DOCUMENTS

JP 58191960 11/1983

(Continued)

OTHER PUBLICATIONS

Hwang, I.S. and Ballinger, R:G., "A Multi-frequency AC Potential Drop Technique for the Detection of Small Cracks," Measurement Science and Technology, vol. 3 (1992), p. 62-74).*

(Continued)

Primary Examiner—Michael Cygan
Assistant Examiner—Punam Patel
(74) Attorney, Agent, or Firm—McNees Wallace & Nurick LLC

(57) ABSTRACT

Instrumentation for monitoring crack growth using a change in electric potential across a starter crack as the crack propagates is disclosed. The instrumentation includes a specimen of a material to be analyzed for crack growth propagation having a surface with a starter crack formed therein, a plurality of current leads to pass electric current through the specimen, a layer of insulating material disposed on each of opposite sides of the crack, a layer of conductive material disposed on each layer of insulating material, where a portion of each layer of conductive material is in electrical contact with the first specimen surface, and a pair of sensing leads, one sensing lead attached to each layer of conductive material. A method for using the instrumentation to monitor crack growth by measuring is also disclosed.

22 Claims, 3 Drawing Sheets

U.S. PATENT DOCUMENTS

| | | | |
|---|---|---|---|
| 4,924,708 A | | 5/1990 | Solomon et al. |
| 5,193,402 A | | 3/1993 | Reed |
| 5,202,641 A | * | 4/1993 | Unvala ................ 324/715 |
| 5,227,731 A | * | 7/1993 | Prabhakaran et al. ....... 324/718 |
| 5,351,026 A | * | 9/1994 | Kanbara et al. ........... 338/22 R |
| 5,837,886 A | * | 11/1998 | Nakahara et al. .......... 73/31.06 |
| 5,911,158 A | | 6/1999 | Henderson et al. |
| 5,952,836 A | | 9/1999 | Haake |
| 5,969,260 A | | 10/1999 | Belk et al. |
| 6,077,418 A | | 6/2000 | Iseri et al. |
| 6,172,511 B1 | * | 1/2001 | Nicholls et al. ........... 324/713 |
| 6,189,767 B1 | * | 2/2001 | Haspeslagh .............. 228/123.1 |
| 6,218,846 B1 | | 4/2001 | Ludwig et al. |
| 6,240,786 B1 | | 6/2001 | Akiyama et al. |
| 6,360,600 B1 | | 3/2002 | Kuroki et al. |
| 6,476,624 B1 | * | 11/2002 | Chuman et al. ........... 324/718 |
| 6,508,129 B1 | | 1/2003 | Sittler |
| 6,516,671 B2 | | 2/2003 | Romo et al. |
| 6,520,020 B1 | | 2/2003 | Lutz et al. |
| 6,532,825 B1 | * | 3/2003 | Abe ........................... 73/804 |
| 6,863,209 B2 | * | 3/2005 | Rinne et al. ................ 228/194 |
| 2002/0092896 A1 | * | 7/2002 | Makino et al. ............. 228/245 |
| 2006/0033504 A1 | * | 2/2006 | Barber et al. ............... 324/523 |

FOREIGN PATENT DOCUMENTS

| | | | |
|---|---|---|---|
| JP | | 63018239 | 1/1988 |
| JP | | 4186102 | 7/1992 |
| JP | | 63223554 | 9/1998 |
| JP | | 11132988 A | * 5/1999 |
| JP | | 2002098626 A | * 4/2002 |

OTHER PUBLICATIONS

R.O. Ritchie et al. Crack-Growth Monitoring: Optimisation of the Electrical Potential Technique Using an Analogue Method. International Journal of Fracture 7.4 (1971): 462-467. Aug. 23, 2006.*

Standard Test Method for Measurement of Fatigue Crack Growth Rates, ASTM Method E647, ASTM International, 100 Barr Harbor Drive, P.O.Box DC700, West Conshohocken, PA 19428 (43 pages).

Lepicovsky, J.; Bruckner, R.J.; and Smith, F.A.: "Thin-Film Thermocouples Technology Demonstrated for Reliable Heat Transfer Measurement"; Application of Thin-Film Thermocouples to Localized Heat Transfer Measurements, AIAA Paper 995-2834 (NASA TM-107045), 1995 (3 pages).

Lisa C. Martin, John D. Wrbanek, and Gustave C. Fralick, Glenn Research Center, Cleveland, Ohio, "Thin Film Sensors for Surface Measurements" NASA/TM—2001-211149, Sep. 2001 (12 pages).

H.H. Johnson, Calibrating the Electric Potential Method for Studying Slow Crack Growth, Materials Research & Standards, Sep. 1965, pp. 442-445 (4 pages).

* cited by examiner

INSTRUMENTATION AND METHOD FOR MONITORING CHANGE IN ELECTRIC POTENTIAL TO DETECT CRACK GROWTH

FIELD OF THE INVENTION

The present invention is directed to instrumentation and methods for measuring crack growth during fatigue testing of materials and is more particularly directed to instrumentation and methods for measuring crack growth during fatigue testing of materials by measuring a change in electric potential across a crack using thin films of insulators and conductors to attach leads to the materials being tested.

BACKGROUND OF THE INVENTION

Machines, particularly machines with rotating parts, such as gas turbine engines, typically undergo cyclic loading during operation. Over time, thermal and mechanical stresses resulting from cyclic loading may cause machine components to fatigue and develop cracks. The rate at which cracks develop and propagate has a direct impact on the lifetime of machine components. By monitoring the growth of cracks on test specimens of machine components, it may be possible to better estimate the useful lifetime of machine components.

One method of monitoring the rate of crack growth measures a change in electric potential across a pre-established crack in a test specimen carrying an electric current, such as provided in ASTM Method E647. The test specimen is then subjected to high temperatures and stresses that replicate the environment inside a working machine. As the crack propagates under the intense thermal environment and stresses, the voltage across the crack increases. This change in electric potential can be measured using two sensing leads placed on either side of the crack.

Instrumentation for monitoring crack growth 100 is shown in FIG. 1, a cross-sectional view. The instrumentation 100 includes a test specimen 110. A starter crack 120 is created in the test specimen 110. Current leads 140, 141 are welded to the test specimen 110. Sensing leads 130, 131 are attached to the test specimen by tack welds 125, 126. The current leads 140, 141 are attached to a standard direct current (DC) or alternating current (AC) source (not shown), while the sensing leads 130, 131 are attached to a voltmeter or other similar device (not shown) to measure the voltage change across the starter crack 120. The test specimen is exposed to conditions which attempt to replicate service conditions, which include high temperatures and stresses. Any growth in the starter crack 120 caused by these conditions causes a change in potential across the starter crack 120 which can be detected using the sensing leads 130, 131.

One problem associated with conventional instruments, such as the one shown in FIG. 1, is that even if the sensing leads are attached to the surface of the specimen with a only a low power weld, some small cracks or weak spots result in the specimen at the welds which invalidates test results. The ability to measure crack propagation is limited to starter cracks larger than 4 mils deep and 8 mils wide, as interference develops from the weld cracks or defects when the starter crack is smaller than this size, making it difficult or impossible to distinguish between propagation of the starter crack and propagation of the defects associated with the tack welds. Further, the sensitivity with which crack growth can be determined depends upon the distance from the sensing lead to the starter crack. The closer the sensing leads are attached to the starter crack, the more likely that any cracks that form at the welds will be a source of interference in measuring electric potential change and thus growth of the starter crack. Thus, conventional methods of using a change in electric potential to measure crack growth propagation are also limited in the sensitivity at which increments of crack growth can be measured. This physical limitation is undesirable.

Accordingly, it may be desirable to provide instrumentation and methods to monitor the growth of cracks that limit inherent damage to the specimen, which damage interferes with the sensitivity of the instrumentation.

It may also be desirable to provide instrumentation and methods that are more sensitive, with the ability to monitor the growth of particularly small cracks, such as those smaller than about 4 mils deep or 8 mils wide, which may result in the ability to even better predict component lifetime.

SUMMARY OF THE INVENTION

Instrumentation for monitoring crack growth is disclosed. The instrumentation comprises a specimen of a conductive material to be analyzed for crack growth propagation, the specimen having a first specimen surface with a preformed starter crack of a predetermined size therein, a plurality of current leads attached to the specimen, the current leads configured to pass electric current through the specimen, a layer of insulating material disposed on each of opposite sides of the starter crack on a portion of the first specimen surface, a layer of conductive material disposed on each layer of insulating material, wherein a portion of each layer of conductive material is in electrical contact with the first specimen surface, and a pair of sensing leads, one sensing lead attached to each layer of conductive material.

A method for monitoring crack growth in a specimen with a starter crack is also disclosed. The method comprises providing a specimen of a preselected material. The specimen of preselected material is provided with a preformed crack of predetermined size formed in a first surface of the specimen. The method further includes attaching a plurality of leads to the first surface of the specimen. The leads include at least two current leads and at least two sensing leads. One end of each of the at least two current leads are attached to the first surface of the specimen by any suitable known technique. An opposed end of the current leads is attached to a current source, so that an electric current can be applied across the first surface of the specimen. The sensing leads, however, are attached to the first surface of the test specimen so as to minimize the formation of defects in the specimen surface, thereby improving the ability to detect changes in voltage across an advancing and enlarging preformed crack. This is accomplished by a low temperature deposition method. As used herein, the term "low temperature deposition method" means application of material to the surface of the test specimen at a temperature sufficiently low such that no adverse metallurgical reactions occur at the interface between the applied material and the surface of the test specimen that can serve as additional crack initiation sites.

The method of the present invention entails first depositing a thin film of insulating material over a portion of the first specimen and on opposite sides of the predetermined starter crack. Next a thin film or layer of conductive material is applied over a portion of the insulating material but is also applied so that a portion of the layer of conductive material contacts the first specimen surface. A sensing lead is then attached to the layer of conductive material on either side of the crack. Because the specimen is conductive, electric current traverses the specimen. The sensing leads are attached to the layer of conductive material which is in electrical contact with the first specimen surface. The opposite end of each of the sensing leads are connected to a means for measuring electric potential, typically a voltmeter. The sensing leads monitor the voltage across the crack. As the crack size changes, the voltage also changes. However, because the cracks and defects from the prior art attachment welds have been greatly reduced or eliminated, conflicting sources of voltage changes are also eliminated, so that more precise voltage changes can be measured on smaller cracks.

One advantage of the present invention is that it provides instrumentation and methods to measure fatigue cracking without damaging the specimen to be tested in a manner that interferes with the testing.

Another advantage of the present invention is that it provides instrumentation that can be used to obtain a more sensitive measurement of fatigue cracking by measuring crack growth in smaller increments than in current state of the art technology.

Still another advantage of the present invention is that it provides instrumentation and methods for measuring crack propagation of smaller starter cracks than in currently available instruments and methods.

Other features and advantages of the present invention will be apparent from the following more detailed description of exemplary embodiments, taken in conjunction with the accompanying drawings which illustrate, by way of example, the principles of the invention.

BRIEF DESCRIPTION OF THE DRAWINGS

FIG. 2b is a cross-sectional side view of the instrumentation of FIG. 2a.

DETAILED DESCRIPTION OF THE INVENTION

The invention is directed to instrumentation and methods for monitoring electric potential across a predetermined starter crack to detect crack growth of the starter crack in a test specimen that overcomes problems encountered by prior instrumentation and methods. The present invention allows cracks of smaller initial size to be monitored while allowing cracks to be monitored with greater sensitivity, thus measuring smaller growth increments. To overcome the limitations of the prior art and avoid inducing damage to the specimen during preparation, which is a source of limitation seen in the prior art, sensing leads are not attached directly to a test specimen to be studied for crack growth.

According to exemplary embodiments of the present invention, sensing leads are in electrical contact with the specimen to measure a change in electric potential across the crack via a conductive intermediary in the form of a thin film of conductive material. The conductive material is applied over a thin film of insulating material applied to a portion of the surface of the specimen on each side of the starter crack. A portion of the conductive material remains in contact with the specimen surface on both sides of the starter crack. The sensing leads are attached to the conductive material over a region that overlies the insulating material. When the sensing leads are welded or brazed to the conductive material, the thin film of insulating material underneath the film of conductive material prevents heat damage and weakening of the test specimen that might serve as a crack initiation point instead of the starter crack. Current is applied to the specimen using current leads attached at locations remote to the starter crack, and the sensing leads, which are in electrical contact with the surface of the specimen through the conductive material, can monitor the voltage resulting from the imperfection of the surface created by the crack.

Figure 1:
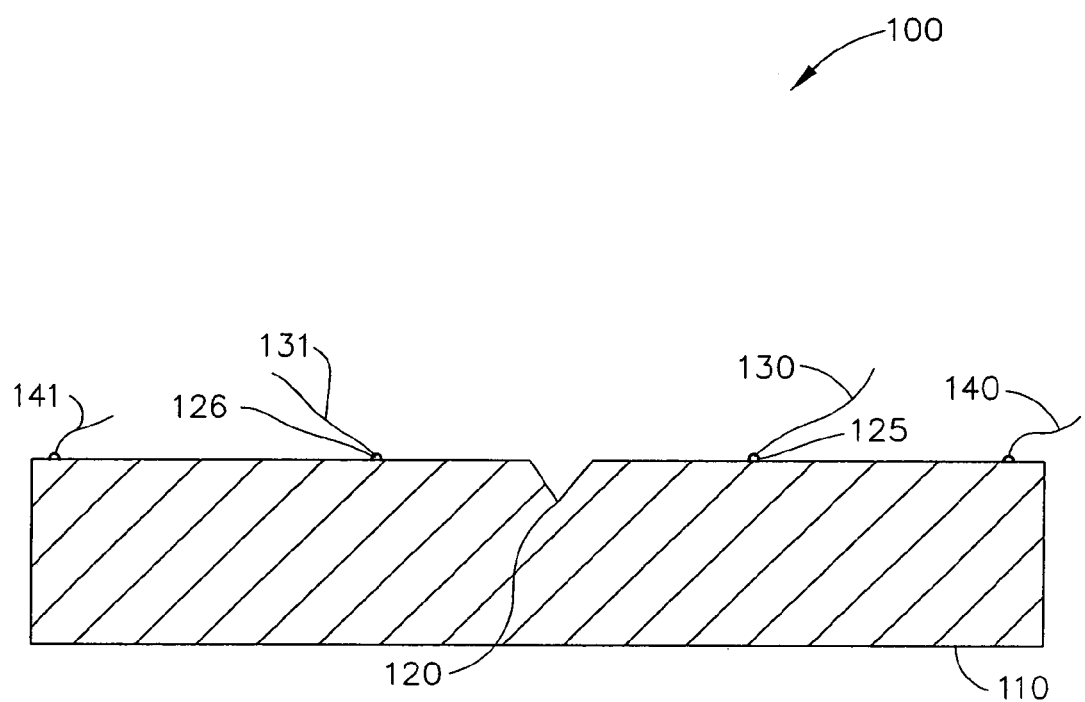
FIG. 1 is a cross-section of conventional instrumentation for monitoring fatigue crack growth using a test specimen.
Figure 2A:
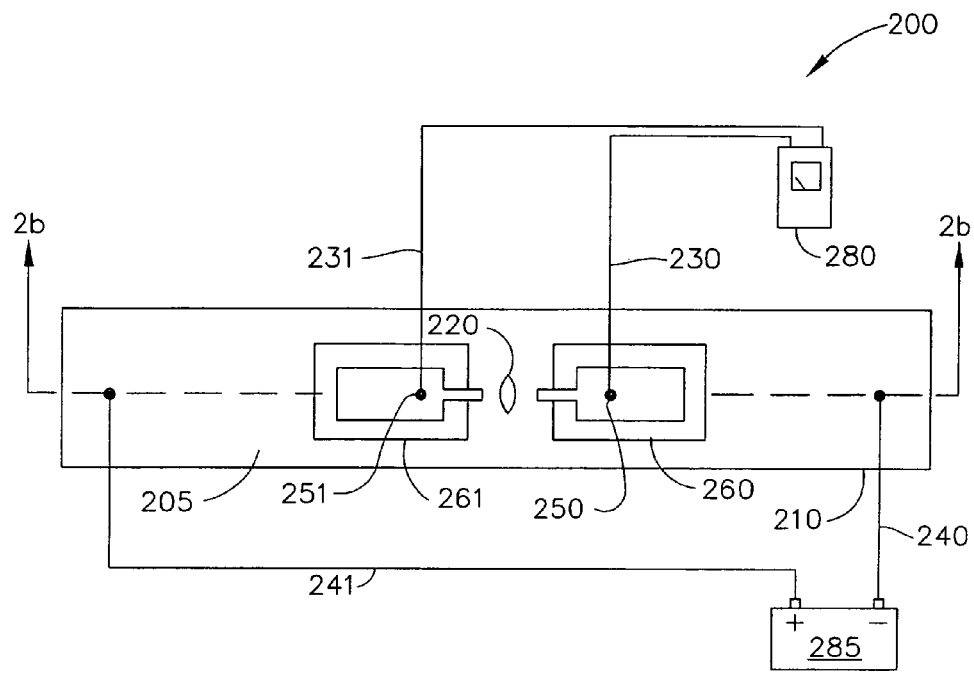
FIG. 2a is a top view of instrumentation for monitoring fatigue crack growth according to an exemplary embodiment of the invention.

Referring to FIG. 2a, instrumentation for monitoring crack growth 200 includes a test specimen 210. A starter crack 220 of predetermined size is created in a surface 205 of the test specimen 210 and extends a preselected depth into the test specimen 210. The starter crack 220 serves as an initiation site from which propagation will occur from fatigue as a result of applied stresses. The preformed starter crack 220 provides the initial site to measure the behavior and rate of crack propagation. Current leads 240, 241 are attached to the test specimen 210 at locations remote from the starter crack 220 to provide a uniform electric current. The starter crack 220, an imperfection in the surface 205, disrupts the current flow and creates an electric potential across the surface 205 of the test specimen 210.

According to embodiments of the present invention, a thin film of insulating material 260, 261 is first applied to a portion of the surface 205 of the test specimen 210 on each side of the starter crack 220. A thin film of conductive material 250, 251 is then applied over the layer of insulating material 260, 261, the layer of conductive material 250, 251 also contacting the surface 205 of the test specimen 210 which is itself conductive. The applied layer of conductive material 250, 251 is continuous across the layer of insulating material 260, 261 to the surface 205 of the test specimen 210. That is, there are no disruptions in the conductive material 250, 251 that would adversely affect the flow of current through the conductive material 250, 251. Sensing leads 230, 231 are then attached to the conductive material 250, 251 overlying the insulating material 260, 261 on either side of the starter crack 220. These sensing leads 230, 231 are also connected to a means for measuring electric potential, preferably a voltmeter 280, to measure a change in electric potential resulting from propagation of the starter crack 220. It will be appreciated that the Figures are for purposes of illustration only and that the items illustrated therein are not meant to represent relative scale.

The test specimen 210 is of a standard size and shape, having a starter crack 220 of predetermined size machined into the surface 205 of the test specimen 210. The test specimen 210 is made of any electrically conductive material for which it may be desirable to measure crack growth. When testing materials for use in gas turbine engines, for example, the test specimen 210 typically comprises a nickel-based, cobalt-based, iron-based, titanium-based, or aluminum-based superalloy or combinations thereof.

The current leads 240, 241 have two opposed ends, one end of each current lead 240, 241 attached to the test specimen 210. The current leads 240, 241 may be attached by any method provided that a reliable connection is made that permits a uniform current to flow through the test specimen 210, but are typically attached by welding at a location remote from the starter crack 220. The current leads 240, 241 are attached in a configuration to pass a DC or AC current through the test specimen 210 when the opposed end of each current lead is attached to a power source 285. The starter crack 220 creates an electric potential on the surface 205 of the test specimen 210, which results when a current is present from the current leads 240, 241. As shown in FIG. 2a, this is preferably achieved by attaching the current leads 240, 241 at opposite ends of the test specimen 210. The current passed through the test specimen 210 via the current leads 240, 241 is typically at least 1 amp, more typically 5 to 50 amps, which is large enough to generate an electric potential across the starter crack 220 to measure crack growth increments at least as small as 0.1 mil. Increases in amperage increase the voltage across the starter crack 220 proportionally, but current larger than 50 amps may be difficult to control and may present a safety hazard.

Sensing leads 230, 231 are used to measure the change in electric potential across the starter crack 220, the electric potential changing with changes in crack size. When the instrumentation 200 is subjected to stress conditions, such as those that replicate service conditions of a gas turbine engine including thermal and operating stresses, the extreme conditions cause fatigue in the test specimen 210, resulting in growth of the starter crack 220 which is evidenced by a change in electric potential across the crack. The sensing leads 230, 231 have two opposed ends, one end attached to the layer of conductive material 250, 251, the opposed end attached to a voltmeter 280. The sensing leads 230, 231 are preferably attached equidistant from the starter crack 220. The voltmeter 280 should be of at least a sufficient sensitivity to measure voltage changes in the range of about 0.1 to 50 millivolts, which are typical of the types of voltage changes using a method according to exemplary embodiments of the invention.

As previously discussed, attaching sensing leads directly to the surface of a test specimen near the starter crack, such as by welding, may result in damage to the specimen that interferes with the ability to accurately measure growth of certain starter cracks, such as those that are smaller than about 4 mils deep and 8 mils wide. The prior art attachment methods, such as those used in ASTM Method E467, produce cracks that cannot be distinguished by the instrumentation from the predetermined starter crack when the starter crack is too small. These cracks resulted from the attachment method itself, such as cracks resulting from thermal stresses of welding sensing leads to the test specimen. This also limited the distance from which the sensing leads could effectively be attached from the starter crack to about 17 mils, limiting the sensitivity of crack growth monitoring to 0.1 mil increments and larger.

The sensing leads carry very little current, and any conductive material may be used as a sensing lead, although a sensing lead that is weldable or brazable, has a melting point well above the test temperature, is oxidation resistant and has sufficient fatigue strength to endure the testing is preferred. Exemplary materials for use as sensing leads include CHROMEL, ALUMEL, gold, silver, platinum, and platinum-rhodium. CHROMEL and ALUMEL are nickel-chrome and nickel-aluminum alloys respectively and are registered trademarks of Hoskins Manufacturing Co. of Hamburg, Mich.

Returning to FIG. 2a, to avoid attaching the sensing lead 230 directly to the surface 205 of the test specimen 210 and avoid damaging the test specimen 210, a thin layer of insulating material 260 is applied to the surface 205 of the test specimen 210 on one side of the starter crack 220, followed by a layer of conductive material 250 applied over the layer of insulating material 260 and in conductive contact with the surface 205 of the test specimen 210. A corresponding layer of insulating material 261, upon which is deposited conductive material 251, is applied to the surface 205 of the test specimen 210 on the opposite side of the starter crack 220. The sensing leads 230, 231 are then attached to the layers of conductive material 250, 251, the sensing leads 230, 231 preferably equidistant from the starter crack 220. Attaching may include, for example, gentle welding methods like capacitive discharge or parallel gap welding or may include brazing or other known forms of attachment made at attachment points 225, 226 such that a sensing lead is attached on each side of the starter crack 220.

While embodiments of the invention will continue to be discussed in the singular, it will be appreciated that this discussion is equally applicable to the layers of insulating and conductive material on both sides of the starter crack 220.

Figure 2B:
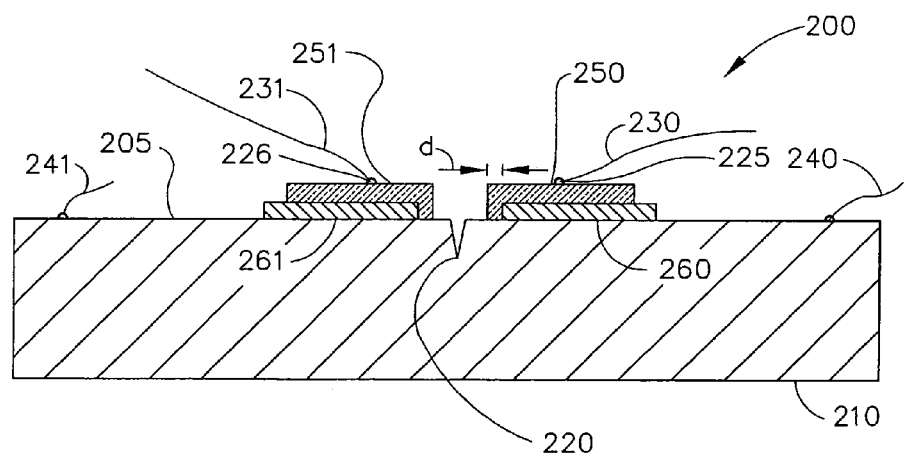

As seen in the cross-sectional side view of the instrumentation 200 shown in FIG. 2b, the sensing lead 230 is in electrical contact with the test specimen 210 by way of the layer of conductive material 250. While the layer of conductive material 250 is disposed over the layer of insulating material 260, at least a portion of the layer of conductive material 250 is in electrical contact with the test specimen 210 so that the sensing lead 230 can be used to measure even small changes in electric potential resulting from small dimensional changes in the starter crack 220. The sensing lead 230 is attached to the layer of conductive material 250 at an attachment point 225, the location of which overlies the layer of insulating material 260.

Typically, the distance from the edge of the portion of the layer of conductive material 250 in contact with the test specimen 210, designated in FIG. 2b as "d," is about 17 mils or less from the starter crack 220. Preferably, the distance between the conductive material and the starter crack 220 is less than about 17 mils. By decreasing the distance over which the change in electric potential is measured across the starter crack 220 to less than 17 mils, crack growth increments can be measured that are smaller than the increment of about 0.1 mils measured with conventional instrumentation. Because the sensing lead 230 is attached to the layer of conductive material 250 and not directly to the surface 205 of the test specimen 210 as in prior art methods, the distance between the crack and sensing leads over which the change in electric potential is measured can be decreased without the adverse affects that result by attaching the sensing lead 230 directly to the test specimen 210. It should be appreciated that the actual physical distance of the sensing lead 230 from the starter crack 220 may be no different or even greater than in prior art methods, but the distance over which the sensing lead is used to measure the change in electric potential is decreased via the layer of conductive material 250. Typically, the sensing lead 230 is attached to the layer of conductive material 250 over the layer of insulating material 260.

By proper selection of conductive material and sensing leads, an attachment between the sensing leads and the conductive material can be made that is more compatible than in the prior art of attaching the sensing leads directly to the specimen surface. For example, lower temperature methods such as brazing can be used, resulting in fewer defects. If welding is used as an attachment method, the welding can be between similar metals or metals that are more compatible for welding. Additionally, because the insulative material typically is thermally, as well as electrically, insulative, the insulating material provides a thermal barrier between the attachment point and the specimen surface.

Returning again to FIG. 2b, the layer of insulating material 260 applied over the surface 205 of the test specimen 210 insulates the test specimen 210 from the heat of attachment that would otherwise result in experiment-limiting cracks or weak spots when attaching the sensing lead 230 directly to the surface 205 of the test specimen 210. While the test specimen 210 may experience an overall increase in temperature during sensing lead attachment, the test specimen 210 does not experience the localized stressing at the attachment points that induce weak spots and/or cracking.

The layer of insulating material 260 can be any electrically and thermally insulating material, although selection of an appropriate material may depend upon the testing conditions to which the test specimen 210 will be subjected. For materials used in machines such as gas turbine engines, for example, which operate under severe conditions and thus are analyzed at very high temperatures, an insulating material should be selected that can withstand those test conditions and which adheres well to the surface 205 of the test specimen 210. Typical insulating materials for these applications are zirconia and alumina, preferably alumina, although the choice of insulating material is not so limited. The insulating material 260 selected should adhere well to the test specimen 210 but still be electrically insulative. Thus, the material should be applied to a sufficient thickness that it is electrically an insulator. It is also desirable that the insulating material 260 be thermally insulative.

The layer of insulating material 260 and the layer of conductive material 250 are applied using thin film methods including sputtering, vapor deposition and photolithography. These and other methods are well known to those of ordinary skill in the thin film art with respect to thin film thermocouples and strain gauges, such as found in Lepicovsky, J. et al., "Application of Thin-Film Thermocouples to Localized Heat Transfer Measurements," AIAA Paper 95-2834 (NASA TM-107045), 1995, which is hereby incorporated by reference.

The layer of insulating material 260 should be thick enough to provide a sufficient insulating effect to prevent damage to the test specimen 210 when attaching the sensing lead 230 to the layer of conductive material 250, but thin enough to avoid spalling. Typically, the insulating layer 260 is at least about 1 micron (0.04 mils) and less than about 10 microns (0.39 mils) thick, typically about 5–8 microns (0.20–0.31 mils) thick.

The material selected for the layer of conductive material 250 may be any conductive material, although materials with high melting points, good oxidation resistance, and compatibility with welding and brazing are preferred. Conductive materials that may be used include the same materials used for the sensing leads, as well as other nickel or cobalt based alloys, although other conductive materials may also be used as will be appreciated by those of ordinary skill in the art. The layer of conductive material 250 may be of any thickness, but should be of a sufficient thickness to allow electricity to flow unimpeded, typically about 5 microns (0.20 mils).

Figure 3:
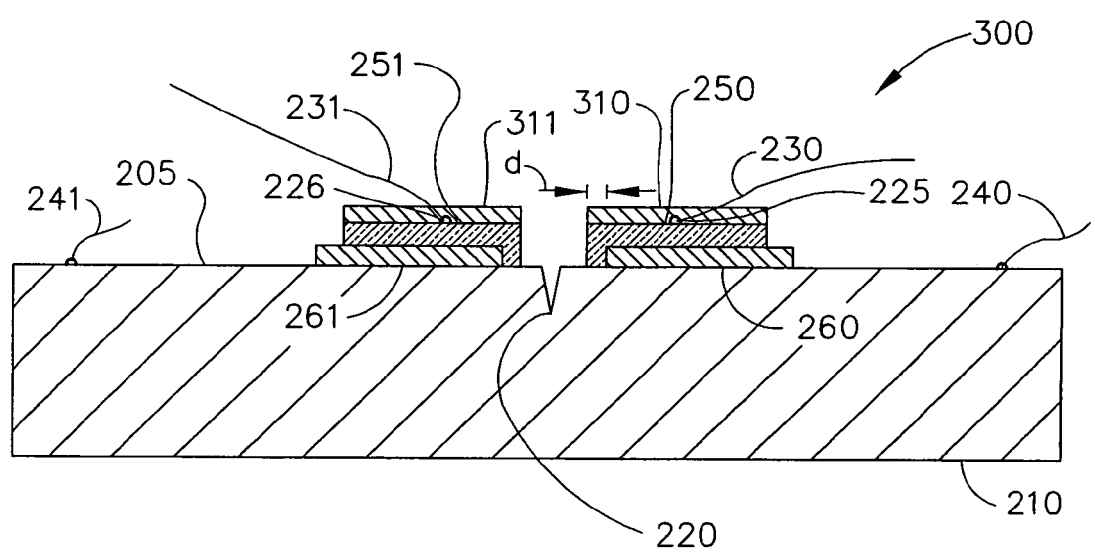
FIG. 3 is a cross-sectional side view of the instrumentation of FIG. 2a in accordance with another embodiment of the invention.

As shown with respect to the instrumentation 300 of FIG. 3, a protective layer 310 comprising alumina may optionally be applied over the conductive layer 250 of the test specimen 210. The protective layer 310 may provide protection from oxidation to the conductive layer 250 which may be advantageous if the test specimen 210 is to be tested under especially harsh conditions that may exceed the normal limitations of even a robust material used in the conductive layer 250. The protective layer 310 may either be applied after the sensing lead 230 has been attached, or prior to attaching the sensing lead 230, provided at least a portion of the conductive layer 250 is left uncovered to provide a location to attach the sensing lead 230.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. Instrumentation for monitoring crack growth comprising:
    a specimen of a conductive material to be analyzed for crack growth propagation, the specimen having a first specimen surface with a preformed starter crack of a predetermined size therein;
    a plurality of current leads attached to the specimen, the current leads configured to pass electric current through the specimen;
    a layer of insulating material disposed on each of opposite sides of the starter crack on a portion of the first specimen surface;
    a layer of conductive material disposed on each layer of insulating material, wherein a portion of each layer of conductive material is in electrical contact with the first specimen surface; and
    a pair of sensing leads, one sensing lead attached to each layer of conductive material.

2. The instrumentation of claim 1, wherein the starter crack has a width of about 8 mils.

3. The instrumentation of claim 1, wherein the starter crack has a depth of about 4 mils.

4. The instrumentation of claim 1, wherein the starter crack has a width shorter than 8 mils.

5. The instrumentation of claim 1, wherein the starter crack has a depth shallower than 4 mils.

6. The instrumentation of claim 1, wherein the layer of insulating material comprises a material selected from the group consisting of alumina, zirconia and combinations thereof.

7. The instrumentation of claim 1, wherein the layer of conductive material comprises a material selected from the group consisting of gold, silver, platinum, rhodium, nickel based alloys, nickel-chrome based alloys, nickel-aluminum based alloys, cobalt based alloys and combinations thereof.

8. The instrumentation of claim 1, wherein the specimen to be analyzed comprises a superalloy selected from the group consisting of nickel-based, cobalt-based, iron-based, titanium-based, aluminum-based and combinations thereof.

9. A method for monitoring crack growth in a specimen having a first specimen surface, the first specimen surface including a starter crack of predetermined size formed therein, the starter crack having opposite sides, the method comprising the steps of:
    applying a layer of insulating material on a portion of the first specimen surface on each of opposite sides of the starter crack;
    applying a layer of conductive material over each layer of insulating material, a portion of each layer of conductive material in electrical contact with the first specimen surface in at least one location;

providing a pair of sensing leads, each sensing lead having opposed ends;

attaching an end of each sensing lead to each layer of conductive material and attaching an opposed end of each sensing lead to a means for measuring electric potential, the sensing leads configured to measure a change in electric potential across the starter crack;

providing at least two current leads, each current lead having opposed ends;

attaching an end of the least two current leads to the specimen, the opposed end of each lead connected to a current source;

passing an electric current through the current leads; and measuring a change in electric potential across the starter crack to monitor changes in the electric potential indicative of growth in the starter crack.

10. The method of claim 9, wherein the portion of each layer of conductive material in electrical contact with the first specimen surface in at least one location is in direct contact with the first specimen surface in at least one location.

11. The method of claim 10, wherein the portion of the layer of conductive material in direct contact with the test specimen applied over the insulating material is about 17 mils from the starter crack.

12. The method of claim 10, wherein the portion of the layer of conductive material in direct contact with the test specimen applied over the insulating material is less than 17 mils from the starter crack.

13. The method of claim 9, wherein the measured change in electric potential across the starter crack is indicative of a crack growth of about 0.1 mil.

14. The method of claim 9, wherein the measured change in electric potential across the starter crack is indicative of a crack growth of less than 0.1 mil.

15. The method of claim 9, wherein the electric current passed through the current leads is at least about 1 amp.

16. The method of claim 9, wherein the electric current passed through the current leads is about 5 to about 50 amps.

17. The method of claim 9, wherein the layer of insulating material is applied to a thickness of about 1 micron to about 10 microns.

18. The method of claim 9, wherein the layer of insulating material is applied to a thickness of about 5 microns to about 8 microns.

19. The method of claim 9, wherein the layer of conductive material is applied to a thickness of about 5 microns.

20. The method of claim 9, wherein the electric current is direct current.

21. The method of claim 9, wherein the electric current is alternating current.

22. Instrumentation for monitoring crack growth comprising:

a specimen of a material to be analyzed for crack growth propagation, the specimen having a first specimen surface with a starter crack formed therein, the starter crack having a width of less than or equal to 8 mils and a depth of less than or equal to 4 mils;

a plurality of current leads attached to the specimen, the current leads configured to pass electric current through the specimen;

a layer of insulating material disposed on each of opposite sides of the starter crack on the first specimen surface;

a layer of conductive material disposed on each layer of insulating material, wherein a portion of each layer of conductive material is in electrical contact with the first specimen surface at a distance of less than or equal to 17 mils from the starter crack; and a pair of sensing leads, one sensing lead attached to each layer of conductive material at a location that overlies the layer of insulating material.

* * * * *